US011793222B2

(12) United States Patent
Beaussoubre et al.

(10) Patent No.: US 11,793,222 B2
(45) Date of Patent: *Oct. 24, 2023

(54) SOLUTIONS AND DISPERSIONS OF AMIDE COMPOUNDS

(71) Applicant: Firmenich SA, Geneva (CH)

(72) Inventors: Pascal Beaussoubre, Geneva (CH); Wolfgang Fieber, Geneva (CH); Howard Munt, Geneva (CH)

(73) Assignee: Firmenich SA, Satigny (CH)

( * ) Notice: Subject to any disclaimer, the term of this patent is extended or adjusted under 35 U.S.C. 154(b) by 816 days.

This patent is subject to a terminal disclaimer.

(21) Appl. No.: 16/070,000

(22) PCT Filed: Feb. 1, 2017

(86) PCT No.: PCT/EP2017/052096
§ 371 (c)(1),
(2) Date: Jul. 13, 2018

(87) PCT Pub. No.: WO2017/134072
PCT Pub. Date: Aug. 10, 2017

(65) Prior Publication Data
US 2019/0104756 A1 Apr. 11, 2019

Related U.S. Application Data

(60) Provisional application No. 62/290,461, filed on Feb. 3, 2016.

(51) Int. Cl.
| | |
|---|---|
| *A23L 27/20* | (2016.01) |
| *A23L 27/00* | (2016.01) |
| *A23L 27/21* | (2016.01) |
| *A23L 27/23* | (2016.01) |
| *A23L 27/26* | (2016.01) |
| *A21D 2/24* | (2006.01) |
| *A23K 20/142* | (2016.01) |
| *A23D 7/005* | (2006.01) |
| *A23L 27/22* | (2016.01) |
| *A23K 20/111* | (2016.01) |
| *A23L 27/24* | (2016.01) |
| *A23K 20/147* | (2016.01) |
| *A21D 2/36* | (2006.01) |
| *A23K 40/10* | (2016.01) |

(Continued)

(52) U.S. Cl.
CPC .............. *A23L 27/204* (2016.08); *A21D 2/24* (2013.01); *A21D 2/36* (2013.01); *A23D 7/0053* (2013.01); *A23D 7/0056* (2013.01); *A23K 20/111* (2016.05); *A23K 20/142* (2016.05); *A23K 20/147* (2016.05); *A23K 20/153* (2016.05); *A23K 40/10* (2016.05); *A23K 50/40* (2016.05); *A23L 27/21* (2016.08); *A23L 27/22* (2016.08); *A23L 27/23* (2016.08); *A23L 27/235* (2016.08); *A23L 27/24* (2016.08); *A23L 27/26* (2016.08); *A23L 27/70* (2016.08); *A23L 27/74* (2016.08); *A23L 27/88* (2016.08); *C07C 233/11* (2013.01); *C07C 235/34* (2013.01); *A23D 7/005* (2013.01); *A23D 9/007* (2013.01); *A23L 2/39* (2013.01); *A23L 3/44* (2013.01); *A23V 2002/00* (2013.01); *A23V 2200/15* (2013.01); *A23V 2200/16* (2013.01); *A23V 2200/238* (2013.01); *A23V 2250/0622* (2013.01); *A23V 2250/302* (2013.01); *A23V 2300/10* (2013.01); *A23V 2300/31* (2013.01)

(58) Field of Classification Search
CPC ........ A23L 27/204; A23L 27/88; A23L 27/21; A23L 27/22; A23L 27/26; A23L 27/24; A23L 27/70; A23L 27/74; A23L 27/235; A23L 27/23; A23L 3/44; C07C 233/11; C07C 235/34; A23V 2002/00; A23V 2200/15; A23V 2200/16; A23V 2200/238; A23V 2250/0622; A23V 2250/302; A23V 2300/10; A23V 2300/31; A23K 20/142; A23K 20/147; A23K 20/153; A23K 40/10; A23K 50/40; A23K 20/111; A23D 7/0053; A23D 7/0056; A23D 7/005; A23D 9/007
USPC ....... 426/534, 535, 536, 537, 538, 650, 465, 426/471

See application file for complete search history.

(56) References Cited

U.S. PATENT DOCUMENTS

2005/0084506 A1  4/2005  Tachdjian et al.
2006/0269610 A1 * 11/2006  Rosenberg ............. A61K 9/146
                                                            424/489

(Continued)

FOREIGN PATENT DOCUMENTS

WO   WO 2013/000673    *  1/2013
WO   2016016276 A1      2/2016

OTHER PUBLICATIONS

International Search Report for PCT Application No. PCT/EP2017/052096, dated Mar. 28, 2017.

(Continued)

Primary Examiner — Leslie A Wong
(74) Attorney, Agent, or Firm — Robert S. Dailey

(57) ABSTRACT

Provided herein is a process for increasing the dissolution rate of a sparingly water soluble flavor or taste modifying compound in water comprising:
a. mixing the compound and a highly water soluble second compound in a water based solution to form a solution or dispersion of the compound; and
b. drying the solution or dispersion to form a solution or solid dispersion of the compound wherein the compound has an increased dissolution rate in water as compared to the compound when dissolved in water alone.

10 Claims, No Drawings

(51) Int. Cl.
    *A23K 50/40*     (2016.01)
    *A23K 20/153*     (2016.01)
    *C07C 233/11*     (2006.01)
    *C07C 235/34*     (2006.01)
    *A23L 2/39*     (2006.01)
    *A23L 3/44*     (2006.01)
    *A23D 9/007*     (2006.01)

(56) References Cited

U.S. PATENT DOCUMENTS

| | | | |
|---|---|---|---|
| 2012/0308703 A1* | 12/2012 | Ley | C11B 9/0069 426/536 |
| 2014/0079783 A1 | 3/2014 | Claudio et al. | |
| 2015/0272185 A1 | 10/2015 | Backes et al. | |

OTHER PUBLICATIONS

Dixit, M. et al., Enhancing the aqueous solubility and dissolution of olanzapine using freeze-drying, Brazilian Journal of Pharmaceutical Sciences, vol. 47, No. 4, 2011, pp. 743-749, XP055355531.

* cited by examiner

SOLUTIONS AND DISPERSIONS OF AMIDE COMPOUNDS

This application is a 371 filing of International Patent Application PCT/EP2017/052095 filed 1 Feb. 2017, which claims the benefit of US provisional patent application 62/290,461, filed 3 Feb. 2016, the contents of which are hereby incorporated by reference in their entirety.

FIELD

The field is related to a delivery system for poorly water soluble compounds such as flavors or taste modifiers.

BACKGROUND

Some flavor molecules are poorly soluble in water. In particular, amides described in Patent Application Number PCT/EP2012/060641, incorporated by reference in its entirety herein, are poorly soluble in water and difficult to solubilize. Hence, it would be advantageous to provide a means for increasing the dissolution rates of these compounds in water.

SUMMARY

Provided herein is a process for increasing the dissolution rate of a sparingly water soluble flavor or taste modifier compound in water comprising:
a) mixing the compound and a highly water soluble second compound in a water based solution to form a solution or dispersion of the compound;
b) drying the solution or dispersion to form a solid dispersion of the compound wherein the compound has an increased dissolution rate in water as compared to the compound when dissolved or dispersed in water alone.

DETAILED DESCRIPTION

For the Summary, Description and Claims, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of".

A compound that is considered sparingly soluble in water is one that is not fully soluble in water above 0.1% or above 1000 ppm (by weight), at 25° C. A water soluble second compound is one that is soluble in water at or above 0.1% or at or above 1000 ppm at 25° C.

In one embodiment, the second compound is a highly water soluble compound that is soluble in water at about ≥0.5% or ≥5000 ppm in water at 25° C.

In one embodiment, the second compound is selected from the group consisting of ribotides, amino acids and MSG, and ingredients that are sources of amino acids and ribotides like yeast extracts, hydrolyzed proteins or peptides. Particularly the second compound is an amino acid and more particularly the second compound is selected from the group consisting of glycine and betaine.

In one embodiment, a process described herein is carried out in the substantial absence of a polymer, particularly less than 5%, 2%, less than 1%, less than 0.5%, less than 0.1%; and no polymer by weight, of the dispersion or solution.

In one embodiment, the water based solution comprises water combined with a volatile water miscible solvent selected from the group consisting of propylene glycol, benzyl alcohol, propanol, ethanol, triacetin, and ethyl citrate.

In one embodiment, the water based solution comprises a water ethanol mixture.

In one embodiment, the ratio, by weight, of the compound to the second compound, by weight, is from 1:99 to 99:1, particularly from 1:19 to about 19:1, more particularly from about 1:10 to about 1:1, particularly about 1:1.

In one embodiment, the sparingly soluble compound is provided in an amount of ≥1% by weight of the total weight of the solution or dispersion; more particularly in an amount of >5% by weight of the total weight of the solution or dispersion.

In one embodiment a water based solution is used wherein the compound and the second compound are dispersed.

In one embodiment a water based solution is used wherein the compound is dispersed and the second compound is dissolved.

In one embodiment water based solution is used wherein the compound and the second compound are dissolved.

In one embodiment, the water insoluble compound comprises a compound of Formula (I)

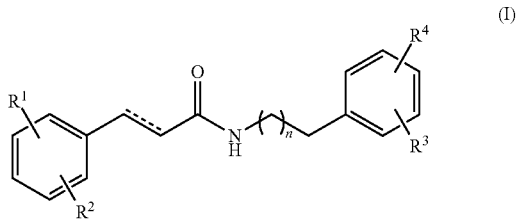

in the form of any one of its stereoisomers or a mixture thereof, and wherein n is an integer from 0 to 2; the dotted line represents a carbon-carbon single or double bond; and each of $R^1$ to $R^4$, when taken independently from each other, represents a hydrogen atom or represents a $R^5$ or $OR^5$ group, $R^5$ representing a $C_1$ to $C_5$ alkyl group; and optionally one of the groups $R_1$ to $R_4$ represents —OH; and/or when $R_1$ and $R_2$ are taken together, and/or $R_3$ and $R_4$ are taken together, represent a $OCH_2O$ group, provided said groups taken together are adjacent substituents of the phenyl group.

In one embodiment, the sparingly soluble compound comprises a compound of formula (II)

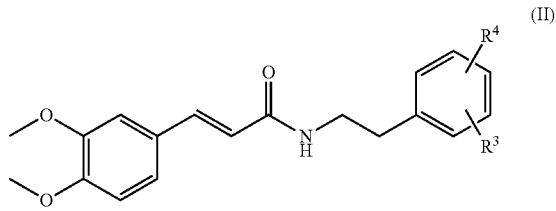

in the form of any one of its stereoisomers or a mixture thereof, and wherein each of $R^3$ or $R^4$, taken independently from each other, represents a hydrogen atom or represents a $R^5$ or $OR^5$ group, $R^5$ representing a $C_1$ to $C_5$, or even a $C_1$ to $C_3$ alkyl group.

In one embodiment, the sparingly soluble compound is selected from the group consisting (E)-3-(3,4-dimethoxyphenyl)-N-(4-methoxyphenethyl)acrylamide, (E)-3-(3,4-dimethoxyphenyl)-N-(3-methoxyphenethyl)acrylamide (E)-3-(3,4-dimethoxyphenyl)-N-(3-ethoxyphenethyl)acrylamide, (E)-3-(3,4-dimethoxyphenyl)-N-(3-propoxyphenethyl)acrylamide, (E)-3-(3,4-dimethoxyphenyl)-N-(4-isopropoxyphenethyl)acrylamide, (E)-3-(3,4-dimethoxyphenyl)-N-(4-ethylphenethyl)acrylamide (E)-3-(3,4-dimethoxyphenyl)-N-(3,4-dimethylphenethyl)acrylamide, (E)-3-(3,4-dimethoxyphenyl)-N-(4-isopropylphenethyl)acrylamide or (E)-3-(3,4-dimethoxyphenyl)-N-(3-methylphenethyl)acrylamide, or (E)-3-(3,4-dimethoxyphenyl)-N-(3,4-dimethoxyphenethyl)acrylamide In one embodiment, the solution or dispersion is lyophilized to form solid particles.

In one embodiment, the solution or dispersion is spray dried to form solid particles.

In one embodiment, the solution or dispersion is dried on a fluidized bed to form solid particles.

In one embodiment a particle provided herein dissolves in water at a rate of up to 20 ppm/min at a temperature of about 60° C., particularly at a rate of 15 ppm/min at a temperature of about 60° C.

In one aspect, the methods provided herein provide increased dissolution rates of a sparingly soluble compound in water. In another aspect, a method provided herein may further enhance the performance of a sparingly soluble compound as a flavor or taste modulator in food and beverage applications.

The types of end products where particles or dry powders provided herein are useful are:
stocks for soup,
any food and beverages applications that require incorporation of hydrophobic actives and fast dissolution and higher active concentration in water.

Compounds of Formula I and II and dispersions provided herein can be used alone or in mixtures and provide a strong kokumi or umami taste at exceptionally low levels.

Provided herein is the use of powders provided herein as a taste-conferring or enhancing ingredient, and in particular to impart or reinforce kokumi or umami taste.

In a particular embodiment of the invention, said compound (I) and (II) is used to impart or reinforce kokumi or umami taste as well as to enhance the saltiness and/or savory perception of a flavor.

Particular applications provided herein are uses to impart or enhance the kokumi or umami taste in savory flavors, such as beef, chicken, pork, and seafood. Surprisingly, in seafood applications such as surimi, or seafood bouillons or snack flavors, compounds according to formula (I) are also found to enhance the perception of sweetness and longevity of the flavor. By contrast, in beef flavors, the compounds according to formula (I) are found to enhance perception of fattiness and tallow notes. Additionally we found that said compounds can increase juiciness in meat based products.

Suitable foodstuff bases, e.g. foods or beverages, can be fried or not, as well as frozen or not, low fat or not, marinated, battered, chilled, dehydrated, instant, canned, reconstituted, retorted or preserved. Typical examples of said foodstuff bases include:
a seasonings or condiment, such as a stock, a savory cube, a powder mix, a flavored oil, a sauce (e.g. a relish, barbecue sauce, a dressing, a gravy or a sweet and/or sour sauce), a salad dressing or a mayonnaise;
a meat-based product, such as a poultry, beef or pork based product, a seafood, surimi, or a fish sausage;
a soup, such as a clear soup, a cream soup, a chicken or beef soup or a tomato or asparagus soup;
a carbohydrate-based product, such as instant noodles, rice, pasta, potatoes flakes or fried, noodles, pizza, tortillas, wraps;
a dairy or fat product, such as a spread, a cheese, or regular or low fat margarine, a butter/margarine blend, a butter, a peanut butter, a shortening, a processed or flavored cheese;
a savory product, such as a snack, a biscuit (e.g. chips or crisps) or an egg product, a potato/tortilla chip, a microwave popcorn, nuts, a pretzel, a rice cake, a rice cracker, etc;
an imitation products, such as a dairy (e.g a reformed cheese made from oils, fats and thickeners) or seafood or meat (e.g. a vegetarian meat replacer, veggie burgers) analogue; or
a pet or animal food.

Particular foodstuffs in which the compound according to formula (I) or (II) find utility include those having flavors such as seafood, beef, chicken, vegetables, cheese, fat, tallow and/or marrow are important.

In one embodiment, an end product is useful as dry, powder form of a taste modifier or flavour in the form of a solid dispersion a sparingly soluble compound, which can be used for example in powder and seasoning blends.

For the sake of clarity, it has to be mentioned that, by "foodstuff" we mean here an edible product, e.g. a food or a beverage. Therefore, a flavored article according to the invention comprises one or more compounds according to formula (I), as well as optional benefit agents, corresponding to taste and flavor profile of the desired edible product, e.g. a savory cube. The nature and type of the constituents of the foodstuffs or beverages do not warrant a more detailed description here, the skilled person being able to select them on the basis of his general knowledge and according to the nature of said product.

The examples provided below are not limiting and are for illustrative purposes only.

EXAMPLES

Example 1

Preparation and dissolution kinetics of solid dispersion of (E)-3-(3,4-dimethoxyphenyl)-N-(4-methoxyphenethyl)acrylamide with glycine according to the invention 1.8 g of (E)-3-(3,4-dimethoxyphenyl)-N-(4-methoxyphenethyl)acrylamide and 1.8 g glycine were mixed with 116 g of a mixture of ethanol and water (50:50 w/w). The dispersion was heated to 60° C. until complete dissolution of the solid material. A clear and transparent solution was obtained. The solution was kept at 60° C., spray dried, and a fine, white powder was obtained. The loading of (E)-3-(3,4-dimethoxyphenyl)-N-(4-methoxyphenethyl)acrylamide of 50% (w/w) in the solid dispersion was confirmed by NMR spectroscopy.

40 mg of the solid dispersion of (E)-3-(3,4-dimethoxyphenyl)-N-(4-methoxyphenethyl)acrylamide and glycine were dispersed in 1 L of water at 60° C., and the solution was stirred at 200 rpm. The dissolution process was followed on-line by monitoring the UV signal of dissolved (E)-3-(3, 4-dimethoxyphenyl)-N-(4-methoxyphenethyl)acrylamide with UV/Vis spectroscopy (measuring absorbance at 310 nm). The dissolution process yielded 50% of the target concentration of 20 ppm of (E)-3-(3,4-dimethoxyphenyl)-N-(4-methoxyphenethyl)acrylamide (10 ppm) after 1.5 minutes, and 95% (19 ppm) after 17 minutes.

Example 2

Comparative Example 20 mg of (E)-3-(3,4-dimethoxyphenyl)-N-(4-methoxyphenethyl)acrylamide were dispersed in 1 L of water at 60° C. The dissolution process yielded 50% of the target concentration of 20 ppm (10 ppm) after 78 minutes (factor 50 slower compared to example 1). 95% (19 ppm) of the target concentration could not be achieved after 6 hours. The concentration of dissolved (E)-3-(3,4-dimethoxyphenyl)-N-(4-methoxyphenethyl)acrylamide after 6 hours was 15 ppm (75% of target).

Example 3

Preparation and dissolution kinetics of solid dispersion of (E)-3-(3,4-dimethoxyphenyl)-N-(4-methoxyphenethyl)acrylamide with betaine according to the invention 1.8 g of (E)-3-(3,4-dimethoxyphenyl)-N-(4-methoxyphenethyl)acrylamide and 1.8 g betaine were mixed with 116 g of a mixture of ethanol and water (50:50 w/w). The dispersion was heated to 60° C. until complete dissolution of the solid material. The solution was kept at 60° C., spray dried, and a fine, white powder was obtained. 40 mg of the solid dispersion of (E)-3-(3,4-dimethoxyphenyl)-N-(4-methoxyphenethyl)acrylamide and betaine were dispersed in 1 L of water at 60° C. The dissolution process yielded 50% of the target concentration of 20 ppm of (E)-3-(3,4-dimethoxyphenyl)-N-(4-methoxyphenethyl)acrylamide (10 ppm) after 2.5 minutes, and 95% (19 ppm) after 29 minutes.

Example 4

Evaluation of the Umami Effect of the Compound According to the Invention in Hot Water Aqueous solutions containing 20 ppm of (E)-3-(3,4-dimethoxyphenyl)-N-(4-methoxyphenethyl)acrylamide and 40 ppm of a solid dispersion of (E)-3-(3,4-dimethoxyphenyl)-N-(4-methoxyphenethyl)acrylamide and glycine according to the invention (50:50 w/w), respectively, were prepared in hot water. The solutions were presented to 4 trained panelists on a blind test basis after 5 minutes. They were asked to rate the samples for the umami taste intensity from 0 to 10 (0 denoted no umami effect, and 10 denoted very strong umami taste). The sample according to the invention was rated higher in umami intensity (5.0) than the comparative sample (3.8).

Example 5

Evaluation of the Umami Effect of the Compound According to the Invention in Cold Water Aqueous solutions containing 20 ppm of (E)-3-(3,4-dimethoxyphenyl)-N-(4-methoxyphenethyl)acrylamide and 40 ppm of a solid dispersion of (E)-3-(3,4-dimethoxyphenyl)-N-(4-methoxyphenethyl)acrylamide and glycine according to the invention (50:50 w/w), respectively, were prepared in cold water (room temperature). The solutions were presented to 4 trained panelists on a blind test basis after 5 minutes. The sample according to the invention was rated higher in umami intensity (3.4) than the comparative sample (2.5).

Example 6

Evaluation of the Umami Effect of the Compound According to the Invention in Hot Chicken Bouillon Chicken bouillon containing 20 ppm of (E)-3-(3,4-dimethoxyphenyl)-N-(4-methoxyphenethyl)acrylamide and 40 ppm of a solid dispersion of (E)-3-(3,4-dimethoxyphenyl)-N-(4-methoxyphenethyl)acrylamide and glycine according to the invention (50:50 w/w), respectively, were prepared. The bouillons were presented to 4 trained panelists on a blind test basis after 5 minutes. The sample according to the invention was rated higher in umami intensity (6.5) than the comparative sample (5.5).

What is claimed is:

1. A process for increasing the dissolution rate of a sparingly water soluble compound, the method comprising:
   a. mixing a sparingly water soluble compound and a highly water soluble second compound in an aqueous composition to form a solution or dispersion of the sparingly water soluble compound; and
   b. drying the solution or dispersion to form a solid composition comprising the sparingly water soluble compound and the highly water soluble second compound;

wherein the sparingly water soluble compound is a compound of Formula (I):

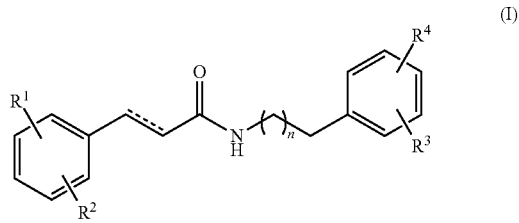

Wherein
   n is an integer from 0 to 2; the dotted line represents a carbon-carbon single or double bond; and each of $R^1$ to $R^4$, when taken independently from each other, represents a hydrogen atom —OH, $R^5$, or an $OR^5$ group, wherein $R^5$ represents a $C_1$ to $C_5$ alkyl group, and no more than one of $R^1$ to $R^4$ is —OH; or $R_1$ and $R_2$ or $R_3$ and $R_4$ combine, when substituting adjacent atoms of the phenyl group, to form an $OCH_2O$ group, provided said groups taken together substitute adjacent carbon atoms of the phenyl group; and
   wherein the highly water soluble second compound is selected from the group consisting of ribotides, amino acids, MSG, and mixtures thereof.

2. The process according to claim 1, wherein the highly water soluble second compound is an amino acid.

3. The process according to claim 2, wherein the amino acid is glycine or betaine.

4. The process according to claim 1, wherein the aqueous composition comprises a volatile water miscible solvent selected from the group consisting of: propylene glycol, benzyl alcohol, propanol, ethanol, triacetin, and ethyl citrate.

5. The process according to claim 1, wherein the aqueous composition comprises water and ethanol.

6. The process according to claim 1, wherein the ratio of the sparingly water soluble compound to the highly water soluble second compound, by weight, ranges from 1:99 to 99:1.

7. The process according to claim 4, wherein the ratio of the sparingly water soluble compound to the highly water soluble second compound, by weight, ranges from 1:19 to 19:1.

8. The process according to claim 5, wherein the ratio of the sparingly water soluble compound to the second highly water soluble compound, by weight, ranges from 1:10 to 1:1.

9. The process according to claim 1, wherein the sparingly water soluble compound is a compound of formula (II)

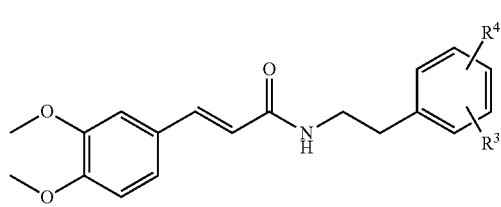

(II)

wherein each of $R^3$ or $R^4$, taken independently from each other, represents a hydrogen atom or represents a $R^5$ or an $OR^5$ group, wherein $R^5$ represents a $C_1$ to $C_5$ alkyl group.

10. The process according to claim 1, wherein the sparingly water soluble compound is selected from the group consisting of; (E)-3-(3,4-dimethoxyphenyl)-N-(4-methoxyphenethyl)acrylamide, (E)-3-(3,4-dimethoxyphenyl)-N-(3-methoxyphenethyl) acrylamide, (E)-3-(3,4-dimethoxyphenyl)-N-(3-ethoxyphenethyl)acrylamide, (E)-3-(3,4-dimethoxyphenyl)-N-(3-propoxyphenethyl)acrylamide, (E)-3-(3,4-dimethoxyphenyl)-N-(4-isopropoxy-phenethyl) acrylamide, (E)-3-(3,4-dimethoxyphenyl)-N-(4-ethylphenethyl) acrylamide, (E)-3-(3,4-dimethoxyphenyl)-N-(3,4-dimethylphenethyl)acrylamide, (E)-3-(3,4-dimethoxyphenyl)-N-(4-isopropylphenethyl)acrylamide, and (E)-3-(3,4-dimethoxyphenyl)-N-(3-methylphenethyl)acrylamide.

* * * * *